United States Patent [19]
Halvorsen et al.

[11] Patent Number: 6,153,432
[45] Date of Patent: Nov. 28, 2000

[54] METHODS FOR THE DIFFERENTIATION OF HUMAN PREADIPOCYTES INTO ADIPOCYTES

[75] Inventors: Yuan-Di Chang Halvorsen, Holly Springs; William O. Wilkison, Bahama, both of N.C.

[73] Assignee: Zen-Bio, Inc, Research Triangle Park, N.C.

[21] Appl. No.: 09/240,029

[22] Filed: Jan. 29, 1999

[51] Int. Cl.[7] ................................ C12N 5/00; C12N 5/02
[52] U.S. Cl. .......................... 435/377; 435/404; 435/405; 435/406; 435/407
[58] Field of Search ..................................... 435/404–407, 435/377

[56] References Cited

U.S. PATENT DOCUMENTS 5,681,561  10/1997  Hirshowitz et al. .................... 424/93.7

OTHER PUBLICATIONS

Sorisky et al., "Evidence of adipocyte differentiation in human orbital fibroblasts in primary culture", J. Clinical Endocrinology and Metabolism 81 (9):3428–31 (1996).
Grimaldi et al., "Trans–differentiation of myoblasts to adipoblasts: triggering effects of fatty acids and thiazolidinediones", Prostaglandins, Leukotrienes and Essential Fatty Acids 57 (1):71–75 (1997).
Teboul et al., "Thiazolidinediones and Fatty Acids Convert Myogenic Cells into Adipose–like Cells", JBC 270 (47):28183–87 (1995).
Tai et al., "Activation of the Nuclear Receptor Peroxisome Proliferator–activated Receptor gamma Promotes Brown Adipocyte Differentiation", JBC 271 (47):29909–14 (1996).
Adams et al., "Activators of Peroxisome Proliferator–activated Receptor gamma Have Depot–specific Effects on Human Preadipocyte Differentiation", J. Clinical Investig. 100 (12):3149–53 (1997).
Gibco Catalog, pp. 101–103, 62 (1992).
Gaillard, et al., "Growth of Preadipocyte Cell Lines and Cell Strains from Rodents In Serum–Free Hormone–Supplemented Medium", In Vitro (1984) Feb., pp. 79–88, vol. 20, No. 2.
Hauner, et al., "Promoting Effect of Glucocorticoids on the Differentiation of Human Adipocyte Precursor Cells Cultured in a Chemically Defined Medium", Journal of Clinical Investigation (1989) Nov., pp. 1663–1670, vol. 84.
Kletzien, et al., "Enhancement of Adipocyte Differentiation by an Insulin–Sensitizing Agent", Molecular Pharmacology (1991) Nov., pp. 393–398, vol. 41.
Kirkland, et al., "Two Preadipocyte Subtypes Cloned from Human Ometal Fat", Obesity Research, (1993) Mar., pp. 88–92, vol. 1.
Cornelius, et al., "Regulation of Adipocyte Development", Annu. Rev. Nutr. (1994) pp. 99–129, vol. 14.
Ailhaud et al., "Adipose Cell Differentiation: A Long Way to Tipperary", Progress in Obesity Research (1996) pp. 3–11, vol. 7.
Marko, et al., "Isolation of a Preadipocyte Cell Line from Rat Bone Marrow and Differentiation to Adipocytes", Endocrinology, (1995) pp. 4582–4588, vol. 136, No. 10.
Digby, et al., "Thiazolidinedione Exposure Increases the Expression of Uncoupling Protein 1 in Cultured Human Preadipocytes", Diabetes, (1998) Nov., pp. 138–141, vol. 47.

Primary Examiner—Sandra E. Saucier
Attorney, Agent, or Firm—Alston & Bird LLP

[57] ABSTRACT

The present invention provides methods and compositions for the consistent and quantitative differentiation of human preadipocytes isolated from adipose tissue into adipocytes bearing biochemical, genetic, and physiological characteristics similar to that observed in isolated primary adipocytes. The methods of the invention comprise incubating isolated human preadipocytes, plated at least about 25,000 cells/cm$^2$, in a medium containing, glucose, a cyclic AMP inducer such as isobutylmethylxanthine or forskolin, a glucocorticoid or glucocorticoid analogue, insulin or an insulin analogue and a PPARγ agonist or a RXR agonist. The compositions of the invention include media for the differentiation of human preadipocytes, human adipocytes differentiated by the methods of the invention and transfected adipocytes.

The present invention also provides methods for determining the ability of a compound to affect the differentiation of human preadipocytes to adipocytes, for determining the ability of a compound to act as a PPARγ antagonist, a glucocorticoid, a glucocoticoid analogue, or an insulin analogue, for transfecting cultured human adipocytes, and as a means to identify novel polypeptides secreted from human adipocytes into the conditioned medium. The methods and compositions have use in the drug discovery of compounds having relevance to the disease states of diabetes, obesity, and cardiovascular disease and in the studies of these diseases.

12 Claims, 6 Drawing Sheets

HUMAN CULTURED PREADIPOCYTES AND HUMAN
CULTURED DIFFERENTIATED ADIPOCYTES.

METHODS FOR THE DIFFERENTIATION OF HUMAN PREADIPOCYTES INTO ADIPOCYTES

FIELD OF THE INVENTION

The invention is drawn to the field of adipocyte biology. Methods and compositions are provided for the differentiation of human preadipocytes into adipocytes.

BACKGROUND OF THE INVENTION

Non-insulin dependent diabetes mellitus (NIDDM) afflicts 4–5 million Americans every year. NIDDM is treated predominately with insulin. However, insulin is not convenient to use in that it must be injected 2–4 times per day and must be stored properly to prevent loss of efficacy. Other drugs used to treat NIDDM include troglitazone (Rezulin™), a PPARγ agonist, Glucophage™ and sulfonylureas. Unfortunately, there are safety concerns related to the use of these drugs. The identification of safe, effective, orally available drugs for the treatment of NIDDM would greatly enhance the quality of life of patients who suffer from this disease. However, studies to find such molecules have been hampered by a lack of reproducible human in vitro cell systems.

Approximately 20–25% of Americans are obese and therefore at increased risk for developing NIDDM, hypertension, and cardiovascular disease. The causes of NIDDM and obesity are often related to defects or problems with adipose tissue. Adipocytes play a critical role in lipid storage and metabolism. Adipocytes also act as endocrine cells to influence physiological parameters such as insulin sensitivity and body weight (Flier, et al., Cell, (1995) 80:15–18)). For example, the ob gene encodes leptin, an adipocyte-secreted endocrine factor (Zhang, et al., Nature (1994) 372:425–432). Leptin has been shown to reduce body weight and blood glucose in obese, diabetic rodents (Pelleymounter, et al., Science, (1995) 269:540–543).

Several adipocyte-specific enzymes and receptors have been shown to be important targets for anti-obesity and anti-diabetic drug discovery. For example, agonists of the β3 adrenergic receptor, which is found predominantly in the adipose tissue in man (Arner, et al., New England Journal of Medicine, (1995) 333:382–383), have anti-obesity and anti-diabetic properties in rodents and are currently in phase II/III trials in man. The thiazolidinedione class of compounds (TZDs), including troglitazone and ciglitazone, has been shown to improve insulin sensitivity and thereby reduce hyperglycemia and hyperlipidemia conditions in rodents and in humans (Saltiel, et al., Diabetes, (1996) 45:1661–1669; Sreenan, et al., American Journal Physiol, (1996) 271:E742–E747; Nolan, et al., New England Journal of Medicine, (1994) 331:1188–1193. Troglitazone (Rezulin™) is approved for use in the U.S. and Japan. Many TZDs, including troglitazone and ciglitazone, are potent activators of Peroxisome Proliferator Activated Receptor gamma (PPARγ), a member of the nuclear receptor family of transcription factors (Tontonoz, et al., Cell, (1994) 79:1147–1156; Lehmann, et al., Journal of Biological Chemistry, (1995) 270:12953–12955). PPARγ is a key regulator of adipocyte differentiation and is most abundant in adipose tissue.

Animal adipocyte studies have been facilitated by the availability of a number of immortalized preadipocyte cell lines such as the 3T3-L1 mouse fibroblast line (Green, et al., Cell, (1974) 1:113–116), which upon proper treatment, will differentiate into adipocytes. These cells have many of the same properties as isolated primary adipocytes. However, recent published reports show that human adipose tissue and adipocytes exhibit significant differences from rodent cells with respect to factors affecting insulin resistance. For example, TNFα appears to be regulated differently in human adipose tissue than in rodent adipose tissue (Hotamisligil, et al., Journal of Clin Invest, (1995) 95:2409–2415). Consequently, studies on human adipocytes and adipose metabolism have been hampered by the lack of a preadipocyte cell culture that can be reproducibly induced to differentiate into adipocytes at high efficiency.

Current protocols for differentiating isolated human preadipocytes result in differentiation frequencies of 5–80%. In these systems, the preadipocyte cell component in human adipose tissue (the so-called "stromal vascular fraction" or SVF) can be isolated using collagenase treatment (Rodbell, Journal of Biol Chem., (1967) 242:5744–5750; Rodbell, et al., Meth Enzymol, (1974) 31:103–14). The isolated human preadipocytes can then be driven to differentiate into adipocytes by a variety of chemical treatments. For example, Hauner's laboratory (Hauner, et al., Journal Clin Invest., (1989) 34:1663–1670) has shown that human preadipocytes can be induced to differentiate in serum-free medium containing 0.2 nM triiodothyronine, 0.5 μM insulin and 0.1 μM glucocorticoid (cortisol, dexamethasone or aldosterone). Under these conditions, differentiation of 5–70% of the preadipocytes was achieved. The percentage of differentiated cells was related to the age of the subject from which the cells were obtained. These investigators claim they can achieve anywhere from 5–70% complete differentiation within 20 days as determined by a variety of biochemical markers. Similarly, O'Rahilly's laboratory (Digby, et al., Diabetes, (1998) 5:138–141) have shown that when the above serum-free medium is supplemented with a TZD such as BRL 49653, differentiation of 20% of omental preadipocytes and 50–80% of subcutaneous and perirenal preadipocytes is achieved.

A method of differentiating human preadipocytes to adipocytes at higher frequency in a shorter period of time and with greater consistency would aid in the study of obesity and diabetes. The present invention provides methods and compositions for the consistent differentiation of 90–95% of human preadipocytes. Several methodologies are provided for different and selective applications.

SUMMARY OF THE INVENTION

The present invention provides methods and compositions for the consistent and quantitative differentiation of human preadipocytes isolated from adipose tissue into adipocytes bearing biochemical, genetic, and physiological characteristics similar to that observed in isolated primary adipocytes. The methods of the invention comprise incubating isolated human preadipocytes, plated at least about 25,000 cells/cm$^2$, in a medium containing, glucose, a cyclic AMP inducer such as isobutylmethylxanthine or forskolin, a glucocorticoid or glucocorticoid analogue, insulin or an insulin analogue and a PPARγ agonist or a RXR agonist. The compositions of the invention include media for the differentiation of human preadipocytes, human adipocytes differentiated by the methods of the invention and transfected adipocytes.

The present invention also provides methods for determining the ability of a compound to affect the differentiation of human preadipocytes to adipocytes, for determining the ability of a compound to act as a PPARγ antagonist, glucocorticoid, glucocorticoid analogue or an insulin analogue, for transfecting cultured human adipocytes, and as a means to identify novel polypeptides secreted from human adipocytes into the conditioned medium. The methods and compositions have use in the drug discovery of compounds having relevance to the disease states of diabetes, obesity, and cardiovascular disease and in the studies of these diseases.

DETAILED DESCRIPTION OF THE INVENTION

The present invention provides methods and compositions for the consistent and quantitative differentiation of human preadipocytes isolated from adipose tissue into adipocytes bearing biochemical, genetic, and physiological characteristics similar to that observed in isolated primary adipocytes. The prior art methods and compositions produce inconsistent differentiation frequencies of 5–80%. See Hauner et al. and Digby et al., supra. In contrast, the methods of the invention reproducibly achieve 90–95% differentiation of cultured human preadipocytes into adipocytes and shorten the culture time from 21 to 12 days.

The compositions of the invention relate to media for the differentiation of human preadipocytes into adipocytes. The compositions of the invention can be used according to the methods of the invention to reliably provide a high differentiation frequency of cultured human preadipocytes. Thus, in one aspect, the invention provides a medium for differentiating human preadipocytes into adipocytes comprising: a defined cell culture medium similar to that described (Ham, *Exp Cell Res.*, (1963) 29:515; Morton, *In Vitro*, (1970) 6:89–108; Dulbecco, et al., *Virology* (1959) 8:396; Smith, et al., *Virology*, (1960) 12:185) having or supplemented with 1.0–4.5 g/liter glucose; a cyclic AMP inducer; 100 nM to 1 μM insulin or an equivalent amount of an insulin analogue; 16 nM to 1 μM of a glucocorticoid; and a concentration of a PPARγ agonist or RXR agonist effective to stimulate differentiation of human preadipocytes.

By "preadipocyte" is meant cells that could be isolated from a stromal vascular fraction prepared from adipose tissue, and that have the potential to differentiate into adipocytes. However, the preadipocytes used in the methods of the invention may be isolated by any means known to those skilled in the art. Preferably, the preadipocytes are isolated from a stromal vascular fraction prepared from adipose tissue.

By a "defined cell culture medium" is meant a serum free, chemically defined cell growth medium. Preferably the medium is Dulbecco's Modified Eagle Medium/Ham's F-10 Nutrient Broth (1:1 v/v) or Earl's medium (Earle, 1943 *JNCI* 4:165–169). However, a variety of media, known to those skilled in the art, are useful in the methods of the invention. Additional compounds may be included or added to the medium. For example, antibiotics, such as penicillin, streptomycin and fungizone are useful additives to the media of the invention. Also, the addition to the media of about 0.5–100 μM biotin, preferably about 10–60 μM biotin, more preferably about 30–35 μM biotin, most preferably about 33 μM biotin; and about 0.5–100 μM pantothenate, preferably 5–50 μM pantothenate, more preferably 15–25 μM pantothenate, most preferably about 17 μM pantothenate, may be useful in promoting cell growth.

The pH of the medium must be maintained at a pH of about 7.0 to 7.6 during use, either through the inclusion of a biological buffer or by adjusting the $CO_2$ content in the atmosphere of the incubator. A "biological buffer" is a mixture of a weak acid and its conjugate base that tends to resist changes in pH when small amounts of acid or base are added. Typical biological buffers include, but are not limited to, phosphate and carbonate buffering systems. Preferably, the medium will be maintained at a pH of about 7.2–7.5, more preferably 7.3 to 7.5, most preferably at a pH of about 7.4. Preferably the medium is buffered by about 15 mM $NaHCO_3$ and about 15 mM HEPES, at a pH of about 7.3–7.5, preferably at a pH of about 7.4.

Fetal bovine serum (FBS) may be added to the defined cell culture medium at a concentration of about 0 to 15%, preferably about 0–10%, most preferably about 3–10%. A concentration of at least about 3% FBS is necessary to ensure that the cells attach firmly to the tissue culture container. However, FBS is not critical for cell differentiation. For example, cells from the stromal vascular fraction may be induced to differentiate into adipocytes in the absence of FBS. In such cases, when changing the media, the cells would have to be recovered by filtration, centrifugation or similar means, since they would not be attached to the culture ware.

By "cyclic AMP inducer" is meant any compound that, in an effective concentration, increases the intracellular concentration of cAMP in a preadipocyte or adipocyte by at least 2%, preferably by at least 5%, more preferably by at least 10%, most preferably by at least 20%. Methods for measuring intracellular cAMP levels are known to those skilled in the art. Preferred cyclic AMP inducers include isobutylmethylxanthine and forskolin. Preferably, the cyclic AMP inducer is 0.2 to 5 mM isobutylmethylxanthine, more preferably, 0.5 to 0.5 mM isobutylmethylxanthine.

By "insulin" is meant any naturally occurring or recombinant mammalian insulin. Preferably the insulin is naturally occurring or recombinant human insulin. By "equivalent amount of an insulin analogue" is meant an amount of a compound that stimulates the differentiation of human stromal vascular cells to adipocytes, using the methods and media of the invention, to the same degree as does 100 nM to 1 µM human insulin. Such insulin analogues may or may not be structurally related to insulin and may be naturally occurring synthetic or recombinant. The percentage of preadipocytes that differentiate into adipocytes may be quantitatively determined by a variety of methods known to those skilled in the art. A preferred method is by Oil Red O staining (Green, supra).

By "glucocorticoid" is meant any steroid or steroid-like compounds and functional derivatives thereof, which is capable of inducing the differentiation of preadipocytes into adipocytes, using the media and methods of the invention. Preferably, the glucocorticoid is dexamethasone, hydrocortisone or cortisol. A physiological concentration of glucocorticoid is used. Preferably the concentration of glucocorticoid is about 16 nM to 1 µM, more preferably about 100 nM to 1 µM, most preferably the concentration of glucocorticoid is about 1 µM.

By "PPARγ agonist" is meant a compound capable of activating the peroxisome proliferator-activated receptor gamma (PPARγ) by at least 10% over background. PPARγ activation may be determined by the method described by Lehmann et al. supra. Preferably the PPARγ agonist is a thiazolidinedione of a derivative or analogue thereof. More preferably the PPARγ agonist is BRL 49653, pioglitizone, troglitazone, darglitazone, ciglitazone, AD5075, AD5080, AD4742 or AD4743. Most preferably the PPARγ agonist is BRL 49653 or troglitazone and the concentration of BRL 49653 or troglitazone is about 0.5–1.0 µM. More preferably the concentration of BRL 49653 or troglitazone is about 0.8–1.0 µM, most preferably the concentration is about 1.0 µM.

By "RXR agonist" is meant a compound capable of activating a retinoic acid X receptor (RXR) by at least 10% over background. RXR activation may be determined by the method described by Heyman et al. (1992 *Cell* 68:397–406). Preferably, the RXR agonist is LG1069 or cis-retinoic acid. Preferably the concentration of LG1069 or cis-retinoic acid is about 100 nM to 10 µM, most preferably the concentration is about 1 µM.

By "effective to stimulate the differentiation of human preadipocytes" is meant having at least about the same effect on the ability to stimulate differentiation of human preadipocytes to adipocytes using to the methods of the invention, as does 0.5–1.0 µM BRL 49653. The percentage of preadipocytes that differentiate into adipocytes may be quantitatively determined by a variety of methods known to those skilled in the art. A preferred method is by Oil Red O staining.

The methods of the invention utilize the above media to achieve at least 90%, typically 90–95%, differentiation of cultured human preadipocytes into adipocytes. Thus, it is a further object of the invention to provide methods for differentiating human preadipocytes into adipocytes, comprising:

a) plating isolated human preadipocytes at a density of about 25,000 to 30,000 cells/cm$^2$ in a preadipocyte medium comprising a defined cell culture medium having or supplemented with 1.0–4.5 g/liter glucose;

b) incubating said cells at about 37° C. for about 4–48 hours until said cells are about 95–100% confluent;

c) replacing said preadipocyte medium with a differentiation medium comprising a defined cell culture medium having or supplemented with 1.0–4.5 g/liter glucose, 0.2 to 0.5 mM isobutylmethylxanthine; 100 nM to 1 µM insulin, or an equivalent amount of an insulin analogue; 16 nM to 1 µM of a glucocorticoid; and a concentration of a PPARγ agonist or RXR agonist effective to stimulate differentiation of human preadipocytes;

d) incubating said cells at about 37° C. for about 2–4 days;

e) replacing said differentiation medium with an adipocyte medium comprising a defined cell culture medium having or supplemented with 1.0–4.5 g/liter glucose; 100 nM to 1 µM insulin, or an equivalent amount of an insulin analogue; 16 NM to 1 µM of a glucocorticoid; and f) incubating said cells at about 37° C. for about 1–2 weeks and refeeding said cells with said adipocyte medium at least every 3–4 days; wherein said preadipocyte medium, said differentiation medium and said adipocyte medium are maintained at a pH of about 7.0 to 7.6 when in contact with said cells.

Human adipose tissue from a variety of sources may be processed to produce preadipocytes for the generation of adipocytes. The adipose tissue may be from subcutaneous or perirenal sites. Preferably the adipose tissue is subcutaneous. Liposuction surgery or penniculectomy may provide subcutaneous adipose tissue.

Preadipocytes may be isolated from adipose tissue by a variety of methods known to those in the art. Preferably the preadipocytes are isolated from the stromal vascular fraction by the method of Rodbell (1974), supra.

When initially plating preadipocytes in preadipocyte medium (step a), the cells must be plated at a density of 25,000–40,000 cells/cm$^2$. Preferably the cell density is 25,000–30,000 cells/cm$^2$. Lower density plating of preadipocytes results in an overall lower differentiation percentage. When plated at a density of 25,000 cells/cm$^2$ the preadipocytes are usually confluent after overnight incubation. If cells are not fully confluent at this point, they may be incubated for up to another 24 hours prior to refeeding with differentiation medium. Longer incubations will result in a lower differentiation percentage.

Once the cells have been exposed to differentiation media (step c), they are susceptible to detaching from the plate if the media is either completely removed or quickly added. When the differentiation or adipocyte medium is changed, care should be taken to leave a layer of medium over the cell surface (approximately 30–50 µl/well for a 96-well plate).

Formation of oil droplets, a characteristic of adipocytes, will occur approximately four days after differentiation medium is added. However, there will be some variation related to inter-patient variability and the site from which the preadipocytes were isolated. In general, at least 90%, typically 90–95% of cells, will differentiate under the above conditions.

A further object of the invention is to provide methods for the identification and study of compounds that enhance preadipocyte differentiation to adipocytes. It has been demonstrated that many compounds that enhance the differentiation of preadipocytes to adipocytes play a role in the treatment of diabetes mellitus. For example, compounds such as insulin, glucocorticoids, and peroxisome proliferator activated receptor gamma (PPARγ) activators effect glucose clearance and mediate the differentiation of preadipocytes to adipocytes. Insulin and Rezulin™ (a PPARγ activator) are currently used to treat diabetes in the U.S. Compounds that affect human adipocyte differentiation or lipogenesis may be useful in the treatment of diabetes and obesity. Such compounds include PPARγ agonists, RXR agonists and insulin analogues.

Accordingly, a method is provided for determining the ability of a compound to affect the differentiation of preadipocytes to adipocytes, comprising:

a) plating isolated human preadipocyte cells at a density of about 25,000 to 40,000 cells/cm$^2$ in a preadipocyte medium comprising a defined cell culture medium having or supplemented with 1.0–4.5 g/liter glucose;

b) incubating said cells at about 37° C. for about 4–48 hours until said cells are about 95–100% confluent;

c) replacing said preadipocyte medium with a differentiation medium comprising a defined cell culture medium having or supplemented with 1.0–4.5 g/liter glucose; a cyclic AMP inducer; 100 nM to 1 $\mu$M insulin, or an equivalent amount of an insulin analogue; 16 nM to 1 $\mu$M of a glucocorticoid; and said compound in an appropriate vehicle or vehicle alone;

d) incubating said cells at about 37° C. for about 2–4 days;

e) replacing said differentiation medium with an adipocyte medium comprising a defined cell culture medium having or supplemented with 1.0–4.5 g/liter glucose; 100 nM to 1 $\mu$M insulin, or an equivalent amount of an insulin analogue; and 16 nM to 1 $\mu$M of a glucocorticoid;

f) incubating said cells at about 37° C. for about 1–2 weeks and refeeding said cells with said adipocyte medium at least every 3–4 days; and g) determining the number or percentage of differentiated cells in the cells from step (f) fed at step (c) with said differentiation medium containing said compound;

h) determining the number or percentage of differentiated cells in the cells from step (f) fed at step (c) with said differentiation medium containing said vehicle alone; and i) comparing the number or percentage of differentiated cells from steps (g) and (h);

wherein said preadipocyte medium, said differentiation medium and said adipocyte medium are maintained at a pH of about 7.0 to 7.6 when in contact with said cells.

Any compound may be tested for its ability to affect the differentiation of preadipocytes to adipocytes. Compounds of particular interest include agonists of PPAR$\gamma$ and/or RXR receptors, such as TZDs. Appropriate vehicles compatible with the compound to be tested are known to those skilled in the art and may be found in a current edition of Remington's Pharmaceutical Sciences. Examples of appropriate vehicles include, but are not limited to, DMSO, DMF or ethanol solutions and a variety of aqueous buffers.

A variety of methods known to those skilled in the art may be used to determine the percentage of differentiated cells. Examples of such methods include those that assess biochemical or morphological characteristics, such as lipid deposits and adipocyte-specific proteins or mRNAs. In a preferred method, the cells are fixed in formalin and stained with Oil Red O dye.

In another embodiment, the invention provides a method for determining the ability of a compound to act as a PPAR$\gamma$ antagonist. Thus, the invention provides a method for determining the ability of a compound to act as a PPAR$\gamma$ antagonist, comprising:

a) plating isolated human preadipocyte cells at a density of about 25,000 to 40,000 cells/cm$^2$ in a preadipocyte medium comprising a defined cell culture medium having or supplemented with 1.0–4.5 g/liter glucose;

b) incubating said cells at about 37° C. for about 4–24 hours until said cells are about 95–100% confluent;

c) replacing said preadipocyte medium with a differentiation medium comprising a defined cell culture medium having or supplemented with 1.0–4.5 g/liter glucose; a cyclic AMP inducer; 16 nM to 1 $\mu$M of a glucocorticoid; 100 nM to 1 $\mu$M insulin, or an equivalent amount of an insulin analogue; and a concentration of a PPAR$\gamma$ agonist or RXR agonist effective to stimulate differentiation of a human preadipocytes; and said compound in an appropriate vehicle or vehicle alone;

d) incubating said cells at about 37° C. for about 2–4 days;

e) replacing said differentiation medium with an adipocyte medium comprising a defined cell culture medium having or supplemented with 1.0–4.5 g/liter glucose; 16 nM to 1 $\mu$M of a glucocorticoid; 100 nM to 1 $\mu$M insulin, or an equivalent amount of an insulin analogue; and said compound in an appropriate vehicle or vehicle alone;

f) incubating said cells at about 37° C. for about 1–2 weeks and refeeding said cells at least every 3–4 days with said adipocyte medium; and g) determining the number or percentage of differentiated cells in the cells from step (f) fed at step (c) with medium containing said compound;

h) determining the number or percentage of differentiated cells in the cells from step (f) fed at step (c) with medium containing said vehicle alone; and i) comparing the number or percentage of differentiated cells from steps (g) and (h);

wherein said preadipocyte medium, said differentiation medium and said adipocyte medium are maintained at a pH of about 7.0 to 7.6 when in contact with said cells.

A variety of PPAR$\gamma$ agonists may be used. Preferentially, the PPAR$\gamma$ agonist is a TZD. Preferably the PPAR$\gamma$ agonist is BRL 49653 at a concentration of about 1–500 nM, preferably about 10–100 nM, most preferably about 50 nM.

In yet another embodiment the invention provides a method for determining the ability of a compound to act as a glucocorticoid or glucocorticoid analogue, comprising:

a) plating isolated human preadipocyte cells at a density of about 25,000 to 40,000 cells/cm$^2$ in a preadipocyte medium comprising a defined cell culture medium having or supplemented with 1.0–4.5 g/liter glucose;

b) incubating said cells at about 37° C. for about 4–24 hours until said cells are about 95–100% confluent;

c) replacing said preadipocyte medium with a differentiation medium comprising a defined cell culture medium having or supplemented with 1.0–4.5 g/liter glucose; a cyclic AMP inducer; 100 nM to 1 $\mu$M insulin, or an equivalent amount of an insulin analogue; and a concentration of a PPAR$\gamma$ agonist or RXR agonist effective to stimulate differentiation of a human preadipocytes; and said compound in an appropriate vehicle or vehicle alone;

d) incubating said cells at about 37° C. for about 2–4 days;

e) replacing said differentiation medium with an adipocyte medium comprising a defined cell culture medium having or supplemented with 1.0–4.5 g/liter glucose; 100 nM to 1 $\mu$M insulin, or an equivalent amount of an insulin analogue; and said compound in an appropriate vehicle or vehicle alone;

f) incubating said cells at about 37° C. for about 1–2 weeks and refeeding said cells at least every 3–4 days with said adipocyte medium; and g) determining the number or percentage of differentiated cells in the cells from step (f) fed at step (c) with medium containing said compound;

h) determining the number or percentage of differentiated cells in the cells from step (f) fed at step (c) with medium containing said vehicle alone; and i) comparing the number or percentage of differentiated cells from steps (g) and (h);

wherein said preadipocyte medium, said differentiation medium and said adipocyte medium are maintained at a pH of about 7.0 to 7.6 when in contact with said cells.

In still another embodiment the invention provides a method for determining the ability of a compound to act as an insulin analogue, comprising:

a) plating isolated human preadipocyte cells at a density of about 25,000 to 40,000 cells/cm$^2$ in a preadipocyte medium comprising a defined cell culture medium having or supplemented with 1.0–4.5 g/liter glucose;

b) incubating said cells at about 37° C. for about 4–24 hours until said cells are about 95–100% confluent;

c) replacing said preadipocyte medium with a differentiation medium comprising a defined cell culture medium having or supplemented with 1.0–4.5 g/liter glucose; a cyclic AMP inducer; 16 nM to 1 $\mu$M of a glucocorticoid; and a concentration of a PPAR$\gamma$ agonist or RXR agonist effective to stimulate differentiation of a human preadipocytes; and said compound in an appropriate vehicle or vehicle alone;

d) incubating said cells at about 37° C. for about 2–4 days;

e) replacing said differentiation medium with an adipocyte medium comprising a defined cell culture medium having or supplemented with 1.0–4.5 g/liter glucose; 16 nM to 1 $\mu$M of a glucocorticoid; and said compound in an appropriate vehicle or vehicle alone;

f) incubating said cells at about 37° C. for about 1–2 weeks and refeeding said cells at least every 3–4 days with said adipocyte medium; and g) determining the number or percentage of differentiated cells in the cells from step (f) fed at step (c) with medium containing said compound;

h) determining the number or percentage of differentiated cells in the cells from step (f) fed at step (c) with medium containing said vehicle alone; and i) comparing the number or percentage of differentiated cells from steps (g) and (h);

wherein said preadipocyte medium, said differentiation medium and said adipocyte medium are maintained at a pH of about 7.0 to 7.6 when in contact with said cells.

A number of studies have suggested that compounds that can induce lipolysis in adipocytes may have utility in treating obesity or cardiovascular disease. The adipocytes differentiated according to the methods of the invention are responsive to lipolytic agents such as norepinephrine and isoproterenol, a $\beta$-adrenoreceptor agonist. When stimulated by lipolytic compounds, triglycerides in adipocytes are converted to glycerol and fatty acids. The glycerol is then released from the cells to the medium. Measurement of glycerol in the conditioned medium is an indication of the response of adipocytes to a lipolytic agent. Accordingly, the mature differentiated adipocytes of the invention may be used to identify and study compounds affecting lipolysis. The ability of a compound to stimulate lipolysis in human adipocytes may also be investigated using this system. Upon full differentiation of the adipocytes, compounds can be added to the cell system to determine their ability to stimulate lipolysis via glycerol production. Glycerol concentration may then be determined using standard methods (Barham, et al., *Analyst*, (1972) 97:142).

The ability to introduce exogenous DNA transiently into cultured human adipocytes will enable the investigator to analyze production of proteins in the adipocyte, characterize promoter regions of adipocyte-selective genes, and identify compounds that affect the expression and regulation of both these described systems. In systems used prior to the instant invention, the inability to obtain an enriched (>90%) population of differentiated adipocytes hampered the use of transfecting exogenous DNA for the purposes of analysis of gene expression. The mixture of preadipocytes and adipocytes in varying proportions precludes the precise analysis of gene regulation because of the existence of two cell types. The availability of a relatively pure population of adipocytes allows for the precise and careful analysis of gene expression via the introduction of exogenous DNA. Thus, in still another embodiment, the invention provides transfected adipocytes differentiated from preadipocytes by the methods of the invention. A variety of transfection protocols using agents known to those skilled in the art, such as calcium phosphate (Wigler, et al., *Cell*, (1977) 11:223–231); lipofectin; (Felgner, et al., *Proc Natl Acad Sci USA*, (1987) 87:7413–7417); or Effectene may be used. Alternatively, viral particles that can infect preadipocytes, for example, adenovirus, may be used to introduce DNA into the stromal cells similarly to the protocols described (Becker, et al., *Meth Cell Biol*, (1994) 43:161–189; Meunier-Durmont, et al., *Eur Jour Biochem*, (1996) 237:660–667). The cells are then treated so they differentiate into adipocytes as described above in Example I. An addition of an antibiotic selection marker allows enrichment for cells bearing the introduced genetic material. The derived adipocytes bearing the introduced genetic material may then be used to study gene regulation as described above.

The ability of the adipocyte to function as an endocrine organ has been validated, in part, by the discovery of leptin, a protein secreted almost exclusively by adipocytes which regulated energy homeostasis in mammals. Other examples include the ability of adipocytes to secrete vascular endothelial growth factor, the agouti protein, and angiotensinogen. All of these proteins/peptides have marked effects on wound healing and angiogenesis, obesity, and cardiovascular function, respectively. The invention of a facile human adipocyte culture system allows the systematic identification of proteins and peptides secreted by these cells. Thus, in still another embodiment, the invention provides a method for identifying proteins and peptides secreted from cultured human adipocytes, comprising fractionating the conditioned media of adipocytes differentiated from preadipocytes by the methods of the invention.

The following examples are offered by way of illustration and not by way of limitation.

EXPERIMENTAL

Example 1

Differentiation of Human Preadipocytes Into Adipocytes

Human preadipocytes were isolated from adipose tissue removed by liposuction surgery according to the procedures previously described by Rodbell and Hauner (Rodbell (1967) and (1974); Hauner, supra). Preadipocytes from the stroma-vascular fraction were resuspended in preadipocyte medium (DME-Ham's F-10, 1:1 (v/v), 10% FBS, and penicillin-streptomycin-fungizone) and plated at 25,000 cells/well in each of the wells of a 96 well plate (150 $\mu$l/well). The cells were then placed in a 37° C. 5% $CO_2$ incubator and allowed to settle overnight. The following day, all of the medium was removed and replaced with 150 μl differentiation medium (Dulbecco's Modified Eagle Medium/Ham's F-10 Nutrient Broth (1:1, vol/vol), 15 mM HEPES buffer, pH 7.4, 33 μM biotin, 17 μM pantothenate, 0.2 mM isobutylmethylxanthine, 100 nM insulin, 1 μM dexamethasone, 1 μM BRL 49653 (diluted into medium from a 100× DMSO stock solution), 10% (vol/vol) fetal bovine serum, 60 U/l streptomycin, 60 U/l penicillin and 25 μg/l Fungizone). The cells were maintained on differentiation medium for 3 days. Additional differentiation medium was added as necessary to maintain the proper volume.

120 μl of the medium was removed, taking care to leave a 30 μl layer over the cell surface to prevent the maturing adipocytes from lifting off of the plate surface due to the surface tension created by removal of all the fluid. The cells were than fed with 120 μl adipocyte medium (Dulbecco's Modified Eagle/Ham's nutrient broth F-10 (1:1, v/v), 15 mM HEPES, pH 7.4, 3% fetal bovine serum, 33 μM biotin, 17 μM pantothenate, 100 nM insulin, 1 μM dexamethasone, 60 U/l penicillin, 60 U/l streptomycin and 25 μg/l Fungizone) and incubated at 37° C. The cells were refed with the adipocyte medium every 3–4 days for 14 days. At each feeding, 100 μl of old medium was removed and replaced with 100 μl fresh medium.

Figure 1A:
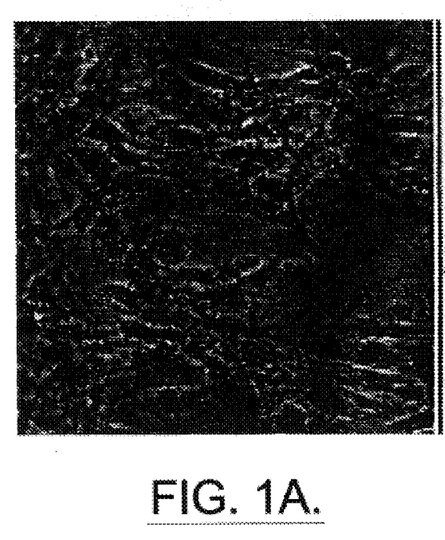
FIG. 1 shows normal human preadipocytes isolated from subcutaneous adipose tissue (Panel A) and human adipocytes differentiated from preadipocytes using the methods described herein (Panel B).
Figure 1B:
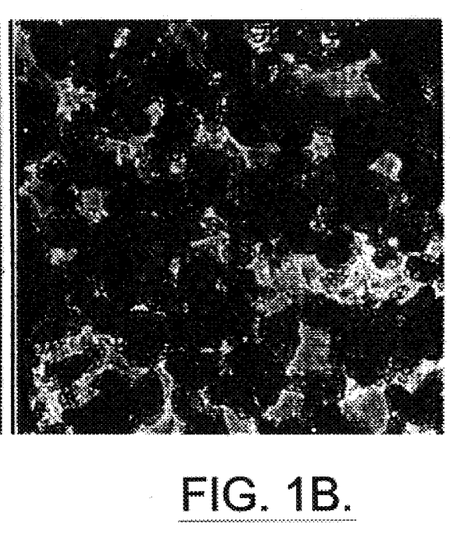

Oil droplets appeared approximately 4 days after differentiation medium was added. Adipocytes could be maintained for one week to three months by re-feeding with adipocyte medium every three to four days. FIG. 1 illustrates the normal and expected morphology observed for preadipocytes and adipocytes stained with oil red O.

The following procedure was used to determine the amount of lipid that had accumulated in the adipocytes. 120 μl/well of medium was removed from each well of the 96-well plates. Care was taken to prevent drying of the wells. 100 μl/well fixer solution (7% formaldehyde in PBS) was added and the plate was incubated at room temperature for at lease 2 hours. Oil Red O working solution was prepared by adding 4 ml distilled water to 6 ml Oil Red O stock solution (1% Oil Red O in isopropanol). The working solution was incubated for 20 minutes at room temperature and then filtered through Nalgene 0.8 μm filter wear. All of the fixer was removed by aspiration until wells were completely dry.

The cells were then incubated with 40 μl/well Oil Red O working solution at room temperature for 10–15 minutes. Care was taken not to touch the sides of the wells in order to prevent high background due to dye stuck on the wall of the well. The plate was covered during incubation to prevent evaporation. Following this incubation, all of the Oil Red O solution was removed and the cells were washed four times with 200 μl/well distilled water. The wash water was drawn off from the top by inserting the manifold or pipette tips to the top of the liquid to remove Oil Red O precipitates floating at the surface. All of the remaining wash water was removed.

Figure 2:
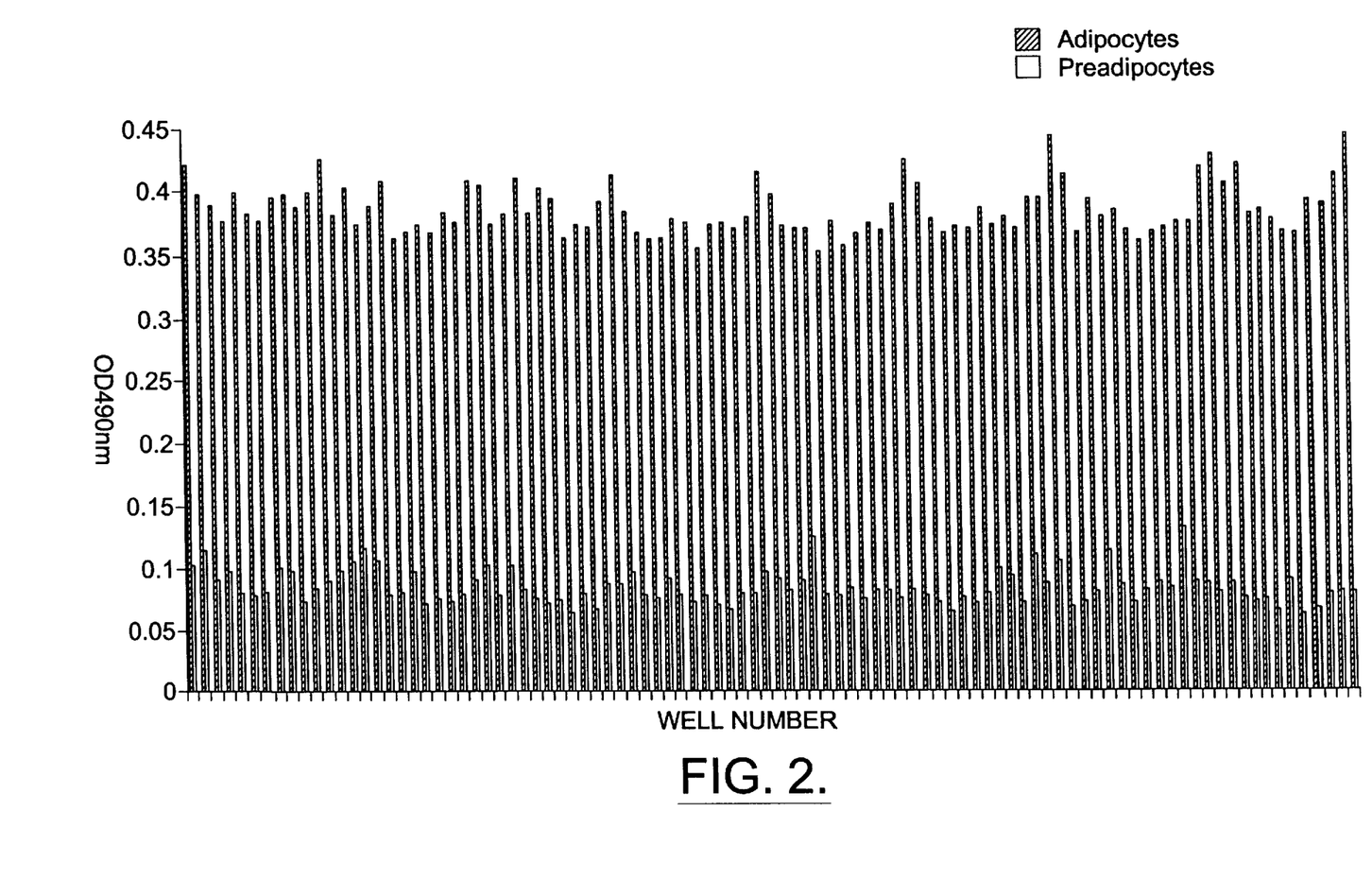
FIG. 2 is a graphical representation of the optical density representing staining with Oil Red O of adipocytes differentiated by the methods of the invention in comparison to the Oil Red O staining of preadipocytes.

Isopropanol (100 μl/well) was then added and the plate was incubated at room temperature for 10 minutes. The isopropanol was pipetted up and down several times, to ensure that all of the Oil Red O was in solution. The optical density was measured at 500 nm. A five-fold increase in staining was observed for differentiated adipocytes as compared to preadipocytes (FIG. 2). The average reading for stained adipocytes was 0.383±0.020 $OD_{500}$. The average reading for the stained preadipocytes was 0.082±0.014 $OD_{500}$. A uniform differentiation of cells in each plate was observed.

Example 2

Figure 3:
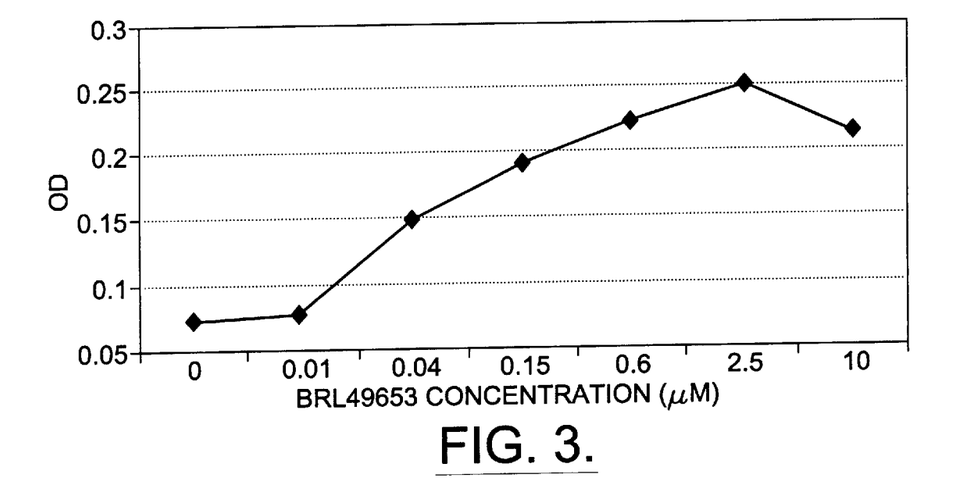
FIG. 3 is a graphical representation of the dose response relationship of BRL49653 in differentiating human preadipocytes.

Identification of Compounds That Enhance Preadipocyte Differentiation to Adipocytes To test the ability of a compound to stimulate differentiation of preadipocytes to adipocytes, the procedures of Example 1 were followed with the following modifications. BRL 49653 was omitted from the differentiation medium and replaced with the compound to be tested or with vehicle alone as a negative control. BRL 49653 was used as a positive control. Various concentrations of BRL49653 in DMEM/F-10 medium containing 3% fetal calf serum, 100 nM insulin, 1 μM dexamethasone, and 0.2 mM isobutylmethylxanthine were incubated with the cells for 3 days and then adipocyte media without BRL49653. After 9 days the cells were washed, fixed and stained with Oil Red O as described herein. The Oil Red O was extracted, quantitated spectrophotometrically and the results plotted as BRL49653 concentration versus optical density (OD). FIG. 3 illustrates the dose responsive effect of BRL49653 on the ability to differentiate human preadipocytes as measured by Oil Red O staining.

Example 3

Identification of Glucocorticoids and Glucocorticoid Analogues

Figure 4:
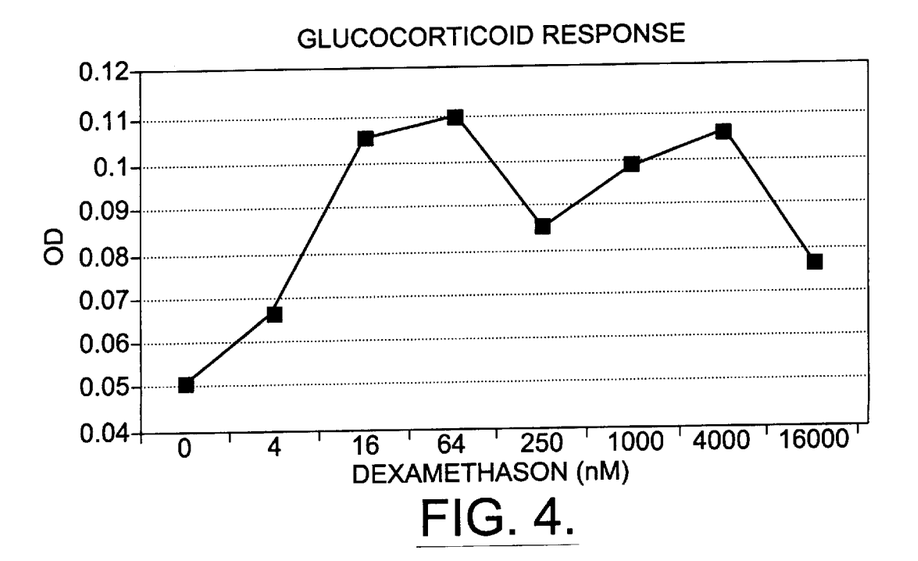
FIG. 4 is a graphical representation of the differentiation of human preadipocytes in response to increasing dexamethasone concentrations.

To test the ability of a compound to act as a glucocorticoid and/or glucocorticoid analogue, the procedures of Example 1 were followed with the following modifications. Human preadipocytes were isolated and cultured in DMEM/F-10 medium containing 3% fetal calf serum, 100 nM insulin, 0.2 mM isobutylmethylxanthine with increasing concentrations of dexamethasone under the conditions described herein for 3 days. The media was then replaced with DMEM/F10 (1:1) containing 3% fetal calf serum, 100 nM insulin and increasing concentrations of dexamethosome. The cells were fed with this medium every three days for 12 days. Cells were then washed, fixed and stained with Oil Red O as described above. FIG. 4 illustrates the ability of dexamethasone to stimulate differentiation in a dose-dependent manner, as measured by lipid accumulation.

Example 4

Identification of PPARγ Antagonists

To test the ability of compounds to act as a PPARγ antagonist, the procedures of Example 1 were followed with the following modifications. The compound to be tested, or vehicle alone as a negative control, was added to the differentiation medium containing BRL49653 at 50 nM, which allows for half maximal stimulation of differentiation. In this case, human preadipocytes were isolated and cultured in DMEM/F-10 medium containing 3% fetal calf serum, 100 nM insulin, 50 nM BRL49653, 1 μM dexamethasone, 0.2 mM isobutylmethylxanthine and 1 μM of a number of novel compounds for 3 days. Cells were incubated with standard adipocyte medium for an additional 10 days. Cells were then washed, fixed and stained with Oil Red O as described.

Figure 5:
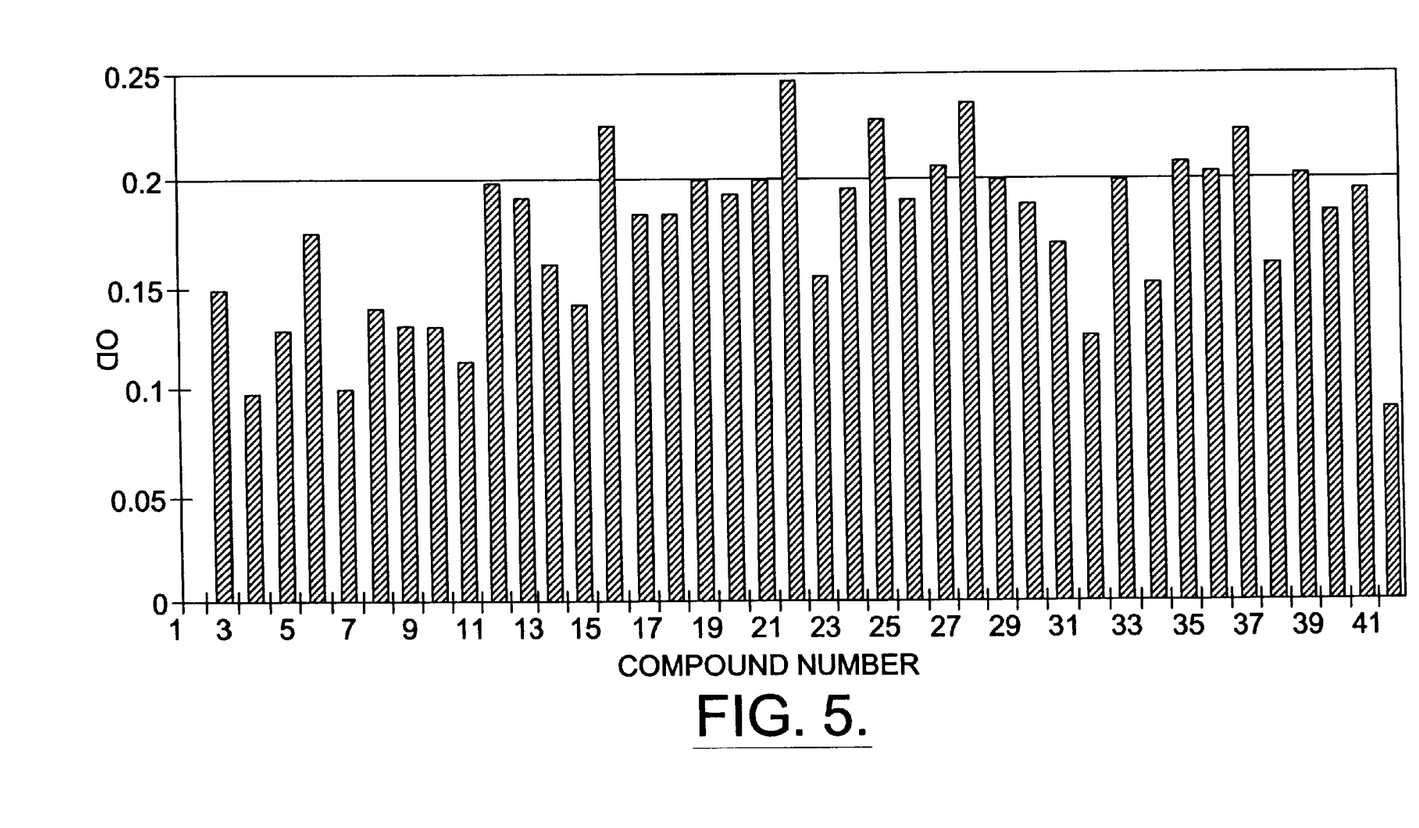
FIG. 5 is a graphical representation of the inhibition of differentiation of human preadipocytes by novel compounds.

FIG. 5 illustrates the screening of a variety of novel compounds at a single dose to determine the ability to inhibit differentiation. The graph shows the optical density plotted versus the various compounds examined. The horizontal line at approximately 0.2 OD is the Oil Red O absorbance observed in the presence of 1 μM BRL49653, which is indicative of 100% differentiation. A number of compounds appear to inhibit half maximal differentiation as measured by Oil Red O staining, since 50 nM BRL4953 yields approximately 0.2 OD units (horizontal line).

Example 5

Identification of Compounds That Induce Lipolysis in Differentiated Adipocytes Preadipocytes from 5 individual patients were isolated and differentiated into adipocytes as described herein. A 96-well plate of adipocytes differentiated by the method in Example 1 was prepared. After 21 days from plating, the cells were washed in Krebs-Ringer buffer and treated with increasing concentrations of isoproterenol. The positive and negative controls (0.5 µM isoproterenol in KRB and KRB alone, respectively) were added in duplicate. The plates were then incubated at 37° C. for four hours.

When lipolytic agents stimulate adipocytes, triglycerides are converted to glycerol and fatty acids. Lipolytic rate was measured in this example by measuring the glycerol released in the medium. At the end of the incubation time, conditioned medium (100 µl) from each well was transferred into a new plate. Glycerol standards (1 mM, 0.5 mM, 0.25 mM, 0.1 mM, 0.05 mM, 0.025 mM, 0 mM) were included.

Figure 6:
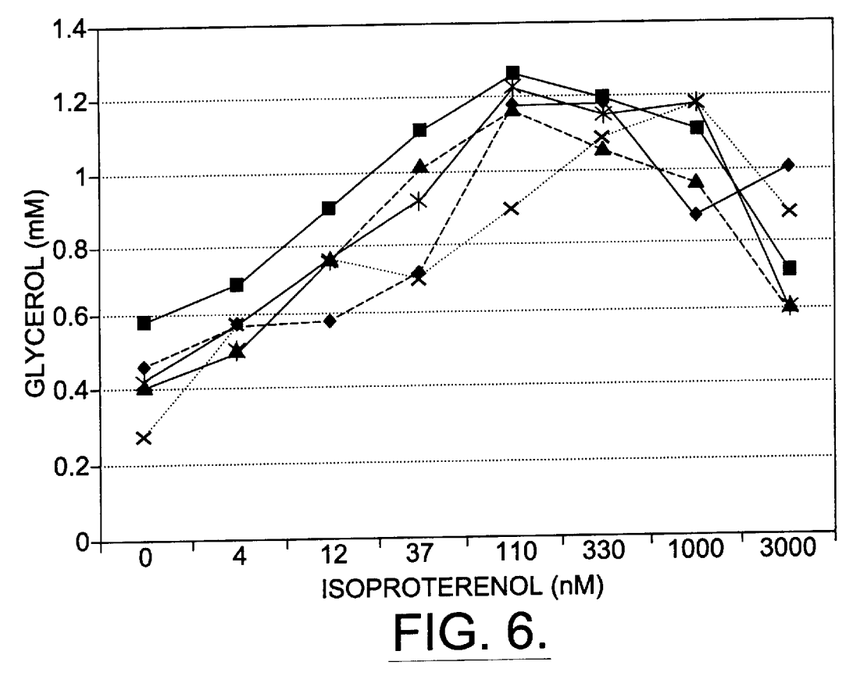
FIG. 6 is a graphical representation of the lipolytic response to isoproterenol of human adipocytes differentiated from preadipocytes isolated from five individuals.

Glycerol assay reagent (100 µl; Sigma glycerol assay kit) was added to each well. The solutions were mixed well and incubated at room temperature for 15 minutes and then the optical density of each well was read at 540 nm. The increase in absorbance at 540 nm is directly proportional to glycerol concentration of the sample FIG. 6 illustrates the ability of a known lipolytic agent, isoproterenol, to dose-dependently stimulate lipolysis in differentiated adipocytes isolated from five different patients.

Example 6

Introduction of DNA Into Adipocytes

Figure 7:
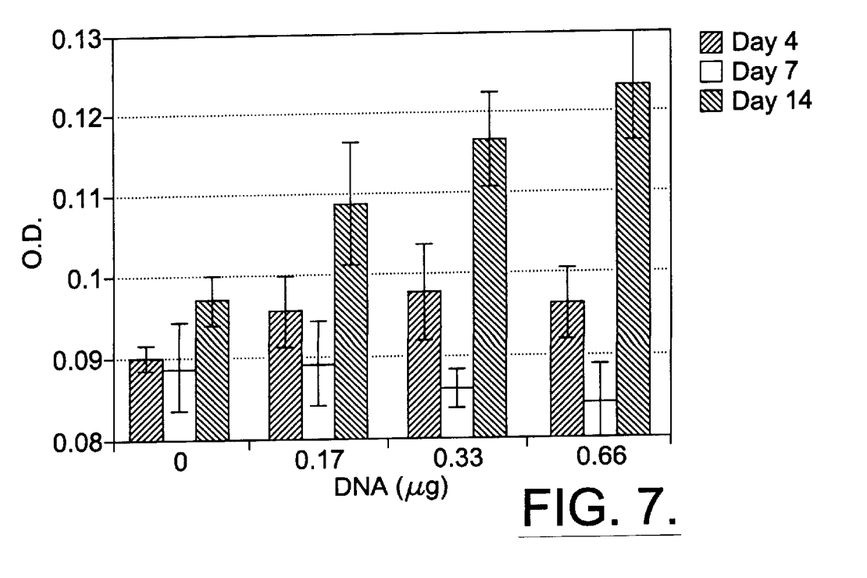
FIG. 7 is a graphical representation of the β-galactosidase expression at 4, 7 and 14 days post-transfection for human differentiated adipocytes transfected with various amounts of pCMV-βgal in the presence of Effectene.

Adipocytes were differentiated from preadipocytes according to the method described in Example 1. 0.1–2.0 µg pCMV-βgal was added to 150 µl of Buffer EC (Qiagen Effectene kit, Catalog number 301425, Qiagen, Valencia Calif.) and then the DNA was allowed to condense in a microcentrifuge tube. 8 µl enhancer (Qiagen Effectene kit) was then added to the DNA mixture, vortexed for one second and allowed to incubate at room temperature for 2–5 minutes. This mixture was centrifuged briefly to remove drops at the top of the tube. 10 µl Effectene reagent was then added, vortexed for 10 seconds, and incubated at room temperature for 5–10 minutes. 120 µl of the old medium was removed (30 µl should be left in the well) from the cells. 70 µl of fresh adipocyte medium was then added. Following a 5–10 minute incubation time, 1 ml of medium was added to the DNA mixture. 25 µl of this final mixture was added to each well. The cells were then incubated for 5 hours. However, Effectene is not toxic and may be left on the cells for any period of time. The cells were then rinsed cells with 80 µl adipocyte medium and then assayed at 72 hours post-infection for β-galactosidase activity. FIG. 7 illustrates the dose-dependence of DNA concentration and the effect of time in culture on the transfection efficiency using Effectene, as measured by β-galactosidase activity.

Example 7

Identification of Novel Proteins From Human Cultured Adipocytes and Preadipocytes The following protocol allows identification of novel proteins from adipocytes prepared according to the methods described in Example 1. Preadipocytes and differentiated adipocytes from the same patient were cultured as described in Example 1 and then incubated in methionine-free adipocyte media for 2 hours. 100 82 Ci$^{35}$[S] methionine was then added to the media and cells were incubated with this mixture for 2 hrs. This media was then replaced with adipocyte media containing a 1 mM non-radioactive methionine chase.

To determine the pattern of secreted proteins, 10 ml of conditioned media was removed from the cells and dialyzed against 4 liters of cold KRB at 4° C. for 4 hrs to remove unincorporated $^{35}$[S]methionine from the radiolabeled proteins. Protein concentration and total radioactivity were determined and 50,000 cpm from each sample was mixed 1:1 vol/vol with a 2× dilution buffer (16% NP-40, 2% ampholines, 8 M urea, 7.5% β-mercaptoethanol, 0.1% bromophenol blue) and immediately loaded onto 12.5 cm long 3% acrylamide gel tube gels containing 8 M urea, 10% NP-40, 5.5% ampholines. Three to four crystals of urea were added to the samples and the tubes agitated until dissolved.

The tubes were placed in an isoelectric focusing chamber with the bottom chamber containing 0.01M $H_3PO_4$ and the top chamber containing 0.02 M NaOH. The samples were run at 12,000 V-hours at constant amperage (0.25 mA/tube). When the voltage increased to 500 volts, the power control was changed to constant voltage. After 12–16 hrs, the voltage was increased to 1000 volts for 3 hours to focus the proteins.

The tube gels were extruded from their cylinders and incubated in equilibration buffer (10% glycerol, 5% β-mercaptoethanol, 0.1 M Tris, pH 6.8, 2% sodium dodecyl sulfate) for 20 minutes. The gradient gel was then placed horizontally onto a 7.5% polyacrylamide gel containing 0.1 M Tris-HCl pH 6.8 and 1% SDS for separation via apparent molecular weight.

Figure 8:
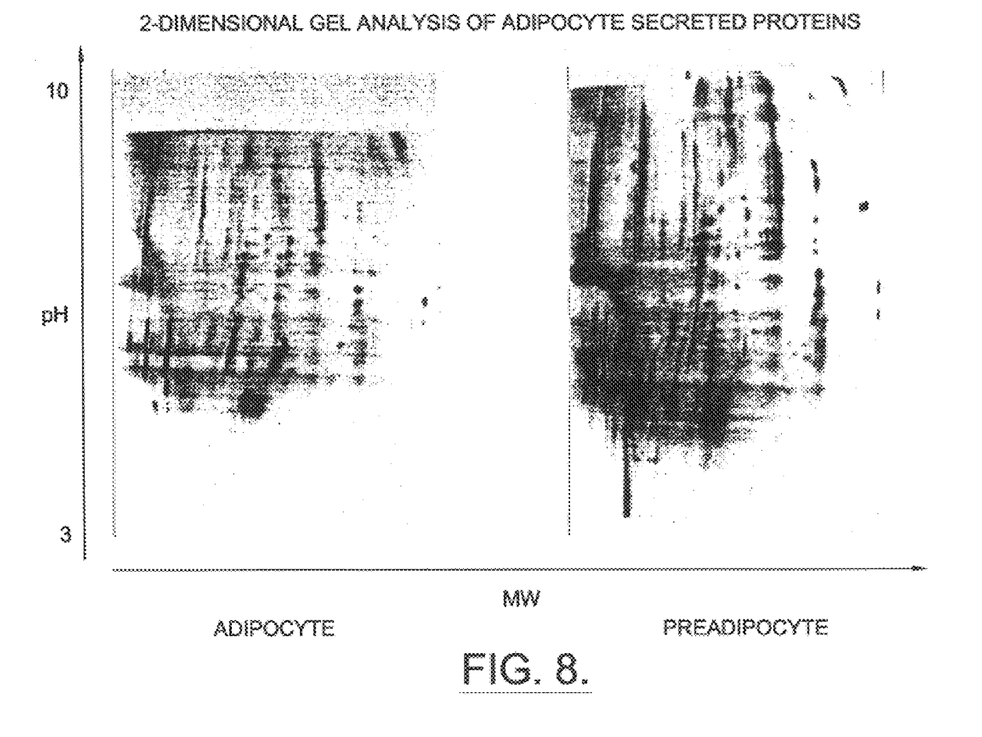
FIG. 8 is an autoradiograph of total human preadipocyte and differentiated adipocyte secreted proteins separated by isoelectric focusing and two-dimensional gel electrophoresis.

The gel was run for 4 hours at 120 volts, removed from the plates and fixed in acetic acid:methanol:water (1:7:2 vol/vol) overnight. The gel was then soaked in a 10% glycerol solution for 20 minutes and dried under vacuum and heat. The dried gel was exposed to x-ray film for 24 hrs to determine the pattern of radiolabeled protein on the gel. FIG. 8 illustrates the patterns observed after labeling secreted proteins from both human preadipocytes (2 days) and differentiated adipocytes (14 days) from the same patient.

All publications mentioned in the specification are indicative of the level of those skilled in the art to which this invention pertains. Publications are herein incorporated by reference to the same extent as if each individual publication was specifically and individually indicated to be incorporated by reference.

Although the foregoing invention has been described in some detail by way of illustration and example for purposes of clarity and understanding, it will be obvious that certain changes and modifications may be practiced within the scope of the appended claims.

What is claimed is:

1. A method for differentiating human preadipocytes into adipocytes, comprising:
    a) plating isolated human preadipocytes at a density of about 25,000 to 30,000 cells/cm$^2$ in a preadipocyte medium comprising a chemically defined cell culture medium having or supplemented with 1.0–4.5 g/liter glucose;
    b) incubating said cells at about 37° C. for about 4–48 hours until said cells are about 95–100% confluent;

c) replacing said preadipocyte medium with a differentiation medium comprising a defined cell culture medium having or supplemented with 1.0–4.5 g/liter glucose, 0.2 to 0.5 mM isobutylmethylxanthine; 100 nM to 1 μM of a glucocorticoid, and a concentration of Peroxisome Proliferator Activated Receptor gamma agonist which is a thiazolidinedione, effective to stimulate differentiation of human preadipocytes;

d) incubating said cells at about 37° C. for about 2–4 days;

e) replacing said differentiation medium with an adipocyte medium comprising a defined cell culture medium having or supplemented with 1.0–4.5 g/liter glucose; 100 nM to 1 μM insulin, or an equivalent amount of an insulin analogue; 16 nM to 1 μM of a glucocorticoid; and f) incubating said cells at about 37° C. for about 1–2 weeks and refeeding said cells with said adipocyte medium at least every 3–4 days; wherein said preadipocyte medium, said differentiation medium and said adipocyte medium are maintained at a pH of about 7.0 to 7.6 when in contact with said cells.

2. The method of claim 1, wherein said preadipocyte medium, said differentiation medium and said adipocyte medium further comprise 3–10% fetal bovine serum.

3. The method of claim 1, wherein said differentiation medium and said adipocyte medium further comprise 1–100 μM pantothenate and 1–100 μM biotin.

4. The method of claim 1, wherein said defined cell culture medium further comprises a biological buffer having a pH of about 7.0 to 7.6.

5. The method of claim 1, wherein said defined cell culture medium is Dulbeccos Modified Eagle/Hams' F-10 Nutrient Broth (1:1 vol/vol).

6. The method of claim 1, wherein said thiazolidinedione is BRL 49653.

7. The method of claim 6, wherein the concentration of said BRL 49653 is 0.5–1.0 μM.

8. The method of claim 1 wherein said thiazolidinedione is troglitazone.

9. The method of claim 8, wherein the concentration of said troglitazone is 1–5 μM.

10. The method of claim 1, wherein said glucocorticoid is dexamethasone, hydrocortisone or cortisol.

11. The method of claim 1, wherein said cyclic AMP inducer is isobutylmethylxanthine or forskolin.

12. The medium of claim 11, wherein said isobutylmethylxanthine is present at a final concentration of about 0.2 to 0.5 mM.

* * * * *